(12) United States Patent
Bellet et al.

(10) Patent No.: US 7,238,519 B2
(45) Date of Patent: Jul. 3, 2007

(54) AUTOMATED IMMUNOASSAY CASSETTE, APPARATUS AND METHOD

(75) Inventors: Neal F. Bellet, Walnut Creek, CA (US); Jeffrey Shindelman, Castro Valley, CA (US); Thomas E. Worthy, Walnut Creek, CA (US); Kimberly Haley, Belmont, CA (US); Richard K-T Lee, Fremont, CA (US); Jane Eunhee Kyung, Sunnyvale, CA (US); Suyue Qian, Fremont, CA (US)

(73) Assignee: Cholestech Corporation, Hayward, CA (US)

( * ) Notice: Subject to any disclaimer, the term of this patent is extended or adjusted under 35 U.S.C. 154(b) by 325 days.

(21) Appl. No.: 11/016,016

(22) Filed: Dec. 17, 2004

(65) Prior Publication Data

US 2005/0147532 A1    Jul. 7, 2005

Related U.S. Application Data

(63) Continuation-in-part of application No. 10/456,230, filed on Jun. 6, 2003.

(60) Provisional application No. 60/387,287, filed on Jun. 7, 2002.

(51) Int. Cl.
*C12M 1/34* (2006.01)

(52) U.S. Cl. .......................  435/287.2; 422/56; 422/57; 422/58; 435/287.7; 435/287.9; 435/805; 435/810; 435/970; 436/514; 436/518; 436/810

(58) Field of Classification Search .................. 422/56, 422/57, 58; 435/287.2, 287.7, 287.9, 805, 435/810, 970; 436/514, 518, 810
See application file for complete search history.

(56) References Cited

U.S. PATENT DOCUMENTS 4,313,734 A    2/1982   Leuvering (Continued)

FOREIGN PATENT DOCUMENTS

WO    WO98/37416 A2    8/1998

(Continued)

OTHER PUBLICATIONS

Chandler, et al., *IVD Technology*, 6(2):37-49 (2000).

(Continued)

*Primary Examiner*—Christopher L. Chin
(74) *Attorney, Agent, or Firm*—Peter J. Dehlinger; Perkins Cole LLP (57) ABSTRACT

An immunoassay cassette, apparatus, and method for detecting an analyte in a liquid body-fluid sample are disclosed. The cassette has a body and a support mounted on the body, for movement relative to the body to first and second transfer positions. Sample supplied to a sample well in the cassette body is transferred to a reagent reservoir on the cassette body, by moving the support to its first transfer position. Here the sample reacts with a first reagent composition in the reservoir effective to form a modified sample. The modified sample is then transferred to a reagent strip on the support by moving the support to its second transfer position. The reagent strip has a transfer zone at which sample material is transferred to the strip, a second reagent composition effective to react with the modified sample to form a detectable analyte-dependent product, and a detection zone located downstream at which the detectable product can be observed. By controlling movement of the support to its first and second positions, the cassette can effectively handle a variety of samples having different flow rates.

16 Claims, 6 Drawing Sheets

U.S. PATENT DOCUMENTS

| | | |
|---|---|---|
| 4,552,839 A | 11/1985 | Gould et al. |
| 4,632,901 A | 12/1986 | Valkirs et al. |
| 4,743,560 A | 5/1988 | Campbell et al. |
| 4,756,828 A | 7/1988 | Litman et al. |
| 4,816,224 A | 3/1989 | Vogel et al. |
| 4,920,046 A | 4/1990 | McFarland et al. |
| 4,943,522 A | 7/1990 | Eisinger et al. |
| 4,956,275 A | 9/1990 | Zuk et al. |
| 4,959,324 A | 9/1990 | Ramel et al. |
| 4,963,468 A | 10/1990 | Olson |
| 4,981,786 A | 1/1991 | Dafforn et al. |
| 4,999,285 A | 3/1991 | Stiso |
| 5,075,078 A | 12/1991 | Osikowicz et al. |
| 5,110,724 A | 5/1992 | Hewett |
| 5,135,873 A | 8/1992 | Becker et al. |
| 5,137,808 A | 8/1992 | Ullman et al. |
| 5,171,688 A | 12/1992 | Hewett et al. |
| 5,252,496 A | 10/1993 | Kang et al. |
| 5,260,221 A | 11/1993 | Ramel et al. |
| 5,559,041 A | 9/1996 | Kang et al. |
| 5,591,645 A | 1/1997 | Rosenstein |
| 5,591,646 A | 1/1997 | Hudson et al. |
| 5,611,995 A | 3/1997 | Groothuizen et al. |
| 5,622,871 A | 4/1997 | May et al. |
| 5,654,162 A | 8/1997 | Guire et al. |
| 5,656,503 A | 8/1997 | May et al. |
| 5,714,389 A | 2/1998 | Charlton et al. |
| 5,744,096 A | 4/1998 | Barr et al. |
| 5,989,921 A | 11/1999 | Charlton et al. |
| 6,027,943 A | 2/2000 | Kang et al. |
| 6,187,598 B1 | 2/2001 | May et al. |
| 6,194,225 B1 | 2/2001 | Oka et al. |
| 6,228,660 B1 | 5/2001 | May et al. |
| RE37,437 E | 11/2001 | Friesen et al. |
| 6,352,862 B1 | 3/2002 | Davis et al. |
| 6,406,920 B1 | 6/2002 | Davis et al. |

FOREIGN PATENT DOCUMENTS

| | | |
|---|---|---|
| WO | WO00/42434 A2 | 7/2000 |

OTHER PUBLICATIONS

De Maat, et al., *Fibrinolysis*, 8(Suppl 2):50-52 (1994).
Grau, et al., *Stroke*, 26(9):1520-1526 (1995).
Kuller, et al, *Am J. Epidemiol.* 144(6):537-547 (1996).
Liuzzo, et al., *N. Engl J. Med.*, 331(7):417-424 (1994).
Mendall, et al, *BMJ* 312(7038):1061-1065 (1996).
Thompson, et al., *N. Engl J. Med.*, 332(7):635-641 (1995).
Tracy, et al., *Circulation*, 93(3):8 (1996).

AUTOMATED IMMUNOASSAY CASSETTE, APPARATUS AND METHOD

This application is a continuation-in-part of U.S. application Ser. No. 10/456,230 filed on Jun. 6, 2003, now pending, which claims benefit of the priority of U.S. Provisional Application No. 60/387,287, filed Jun. 7, 2002, now abandoned, both of which are incorporated herein in their entirety by reference.

FIELD OF THE INVENTION

The present invention is directed to a cassette, apparatus and method for use in assaying a body fluid sample for a selected analyte, and particularly for use in automated multi-stage assays.

REFERENCES

De Maat, M. P. M. et al., *Fibrinolysis* 8 (Suppl 2):50-52 (1994).

Grau, A. J. et al., "Clinical and Biochemical Analysis in Infection-Associated Stroke." *Stroke* 26(9): 1520-1526 (1995).

Harlow, E. et al., "Antibodies: A Laboratory Manual", Cold Spring Harbor Lab (1988).

Hewett, G. E., U.S. Pat. No. 5,110,724 (1992).

Hewett, G. E. et al., U.S. Pat. No. 5,171,688 (1992).

Kuller, L. H. et al., *Am J Epidemiol.* 144:537-5547 (1996).

Leuvering et al., U.S. Pat. No. 4,313,734 (1982).

Liuzzo G, M.D. et al., *N Engl J Med* 331(7):417-424 (1994).

Mendall, M. A. et al., *British Med. J.* 312:1061-1065 (1996).

Thompson, S. G. et al., *N Engl J Med* 332:635-641 (1995).

Tracy, R. P. et al., *Circulation,* 93(3):8 (1996).

BACKGROUND OF THE INVENTION

Assays for detecting the presence and level of a variety of analytes in body fluid samples are known. Such assays are often designed for simplicity of use so that they can be reliably conducted in a doctor's office or other clinical setting where personnel may have little training in clinical assay procedure or in interpreting assay results. In order to minimize the need for operator involvement, it is preferable that the assay be carried out in an automated or self-contained manner.

Such self-contained assays have typically been limited, for the sake of simplicity of operation, to one-step assay procedures. A number of useful assays, however, are multistage in nature, requiring more than one reacting or binding step. Further, one or more of the steps may be rate limiting, or the rate of liquid flow from one assay region to another may be dependent on the nature of the sample. Typically, multistage assays are less readily automated and generally require more input from the user, thus increasing the possibility of error.

It is therefore desirable to provide an automated, self-contained assay device which is able to perform multistage assays, in particular those containing multiple reacting or binding steps in which rates of sample movement within an assay device, or rates of assay reactions are variable, depending on the nature of the sample and the assay being performed.

SUMMARY OF THE INVENTION

The invention includes, in one aspect, an immunoassay cassette for use in detecting an analyte in a liquid body fluid sample. The cassette includes a cassette body having a sample well for receiving the sample, and a reservoir carried on the body and containing a first reagent composition effective to react with one or more sample components to form a modified sample. A support mounted on the body, for movement relative to the cassette body to first and second transfer positions, carries a reagent strip containing a second reagent composition effective to react with the modified sample formed in said reservoir to form a detectable analyte-dependent product. Movement of the support relative to the cassette body to its first transfer position is effective to transfer sample liquid placed in the sample well to the reservoir, and movement of the support to its second transfer position is effective to transfer sample liquid in the reservoir to the reagent strip.

The cassette may further includes a separation layer mounted on the body in liquid communication with the sample well, where the reservoir is mounted on the body for movement to a position of liquid communication with the separation layer, when the support is moved to its first transfer position. The separation layer may be effective to remove blood cells from a blood-cell sample placed in the sample well, as sample liquid flows in the layer from the sample well toward the position at which liquid is to be transferred to the reservoir.

The cassette may further include a liquid-carrying strip carried on the body, abutting one end of the reservoir, and dimensioned to make contact with the reagent strip, for transferring liquid from the reservoir to the reagent strip, when the support is moved to its second transfer position.

For use in detecting a multivalent analyte in a liquid body-fluid sample, the first reagent composition in the reagent reservoir may include a non-immobilized conjugate of an anti-analyte antibody and a detectable reporter group, where the reaction to form a modified sample includes binding of the conjugate to sample analyte, to form an analyte-conjugate complex. The reagent composition in the reagent strip may include an anti-analyte antibody immobilized at a detection region in the reagent strip, where the reaction to form a detectable analyte-dependent product includes binding of complex to the immobilized antibody, to localize the detectable reporter in the complex at the detection zone. The non-immobilized conjugate may be a conjugate of an anti-analyte antibody and a detectable reporter. For use in detecting C-reactive protein analyte in a blood sample, the anti-analyte antibody in the non-immobilized conjugate in the reagent reservoir, and the immobilized anti-analyte antibody in the reagent strip may be specific against a common epitope in C-reactive protein.

The support may include a window through which a detectable reaction at the reaction zone in the reagent pad strip can be viewed. The detection zone in the reagent strip may be covered by a reflective film at the strip's surface facing away from said window, such that flow of sample liquid through the detection zone produces a first change in reflectance measurable through the window, and the presence of analyte-dependent reaction at the detection zone produces a second change in reflectance measurable through the window.

In another aspect, the invention includes an apparatus for use in detecting an analyte in a liquid body-fluid sample. The apparatus includes a cassette of the type described above, and a cassette handling instrument having a cassette holder into which the cassette is removably placed, during a sample assay, an actuator operable to move the support in the cassette to its first and second transfer positions, and a detector operable to detect an analyte-specific reaction at the detection zone in the reagent strip. A control unit in the instrument is operably connected to the actuator, for moving the support in the cassette to its first transfer position, and subsequently to its second transfer position at timed intervals.

In moving the cassette support to its first and second transfer positions, the actuator in the instrument may operate to press on one or more surface regions of the support.

Where the cassette includes a separation layer mounted on the body in liquid communication with the sample well, the reservoir may be mounted on the body for movement to a position of liquid communication with the separation layer, when the support is moved to its first transfer position. In this embodiment, the control unit may be operable to move the support to its first position at a selected time interval $\Delta t_1$ after sample is introduced into the sample well, and to move the support to its second transfer position, at a selected time interval $\Delta t_2$ later, where $\Delta t_1$ is selected to allow sample-liquid flow from the sample well through the separation layer to the position of liquid communication with the reservoir, and $\Delta t_2$ is selected to allow sample-liquid flow from the separation strip into said reservoir. Where the separation layer is effective to remove blood cells from a blood-cell sample placed in the sample well, as sample liquid flows in the separation layer from the sample well toward the position at which liquid is to be transferred to said reservoir, $\Delta t_1$ and $\Delta t_2$ may be selected to have greater values for a sample containing blood cells than one without blood cells.

The control unit may be further operable to move the support, after time interval $\Delta t_2$, toward and away from its second transfer position, to reduce the volume and rate of sample flow from the reservoir to the reagent strip relative to that obtained when the control unit operates to hold the support at its second transfer position. Here the control unit may be operable to control the rate of sample transfer from the reservoir to the reagent strip by controlling (i) the cycle frequency with which the actuator moves the support toward and away from its second transfer position and (ii) the time of contact that the support is held in its second transfer position, during each cycle.

In still another aspect, the invention includes an improvement in an assay device of the type having a body, a well formed in the body for receiving a liquid sample, such as a blood sample, containing cells or other particulates, and an elongate separation strip carried on the body and having a sample-application region overlying such well, such that sample placed in the well is drawn into and through the strip's sample-application region, and sample liquid is separated from sample particles as sample flows through the strip and particle movement in the strip is blocked or retarded.

The improvement includes a channel (i) formed in the device between the strip and a region of the body immediately downstream of the sample well and (ii) by which sample in the sample well can flow the said strip downstream of the sample-application region in the strip. The channel may have a thickness, between the body and strip, of about 2-5 times the size of the sample particles. Thus, for use in assaying an analyte in a blood sample, the channel thickness may be between 5-15 microns.

These and other objects and features of the invention will become more fully apparent when the following detailed description of the invention is read in conjunction with the accompanying drawings.

DETAILED DESCRIPTION OF THE INVENTION

I. Immunoassay Cassette

For convenience, similar element numbering is retained in all the figures to identify like structural features.

Figure 1A:
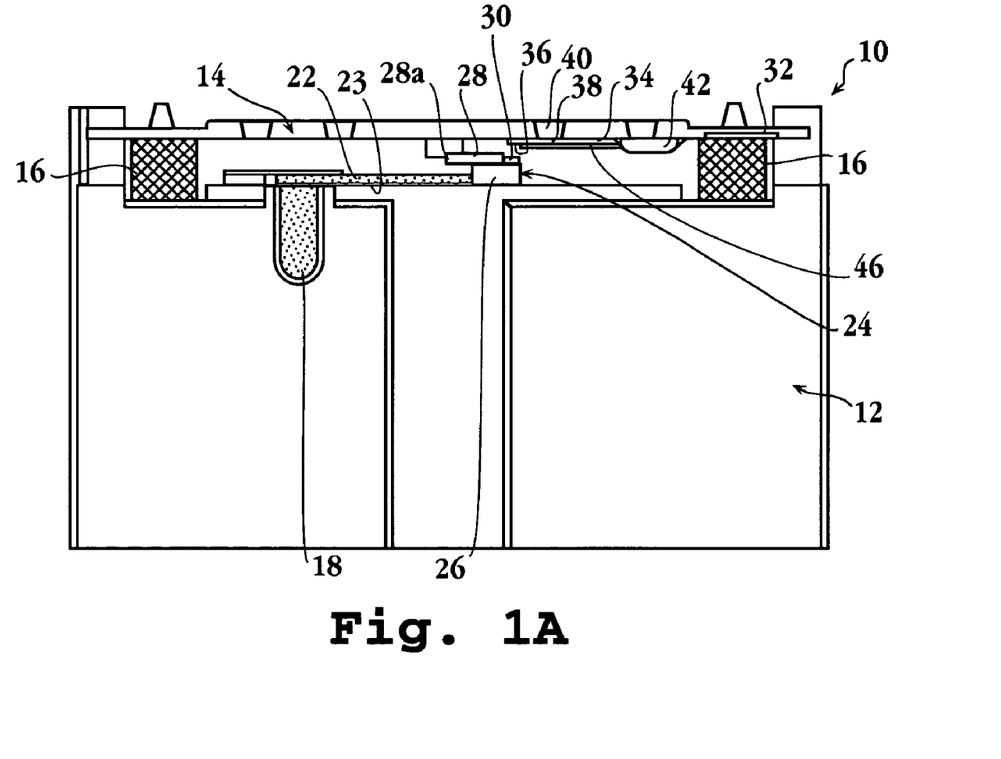
FIGS. 1A, 1B, and 1C are plan views of an immunoassay cassette constructed in accordance with one embodiment of the invention, with the cassette in an initial sample loading position (FIG. 1A), at its first transfer position (FIG. 1B), and at its second transfer position (FIG. 1C)
Figure 1B:
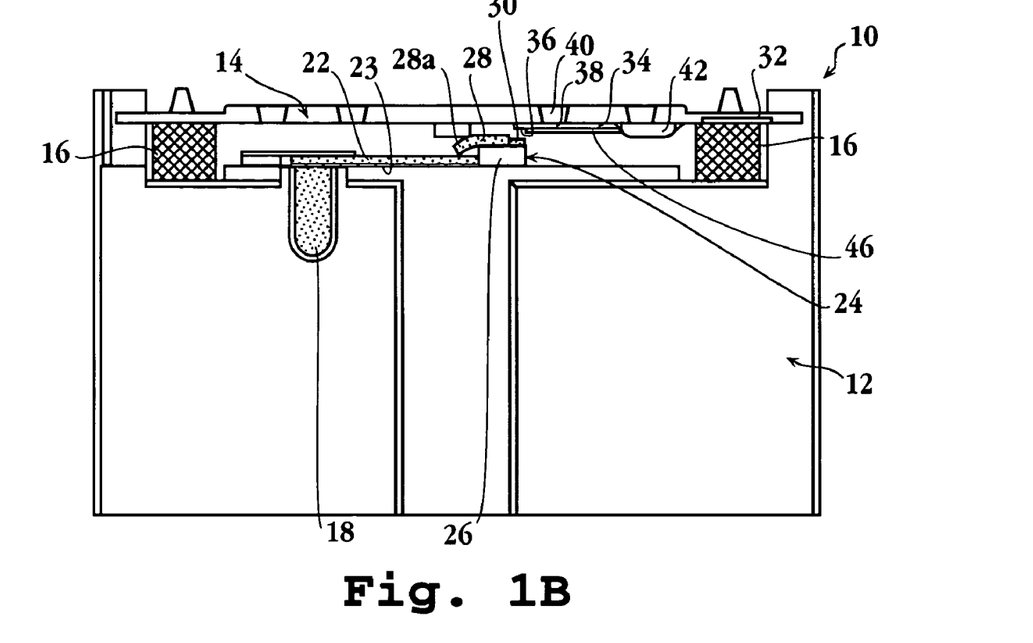
Figure 1C:
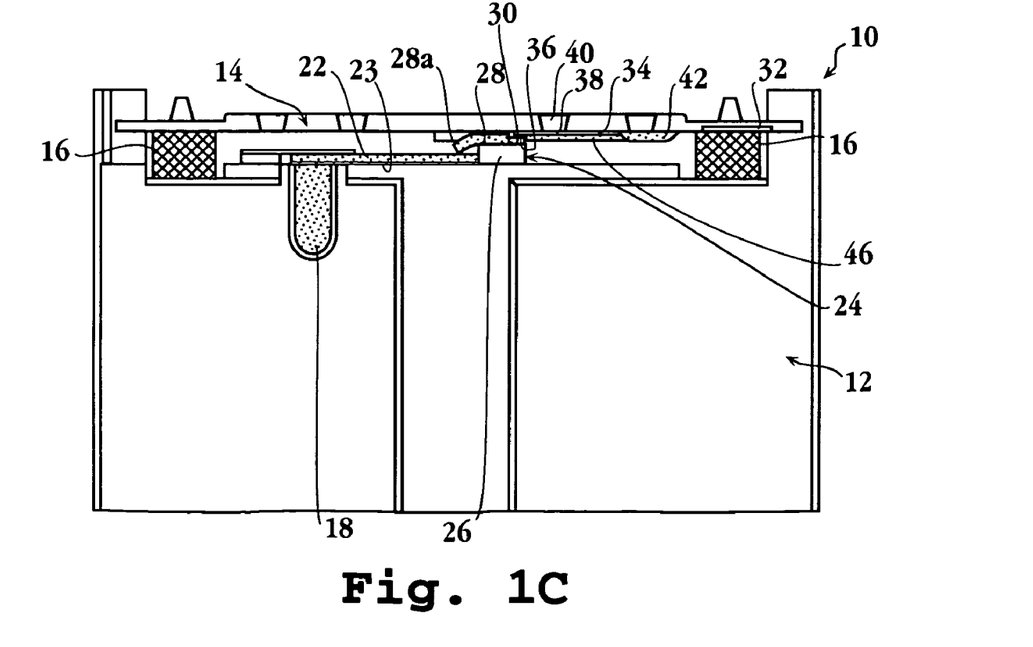

FIGS. 1A-1C show an immunoassay cassette 10 constructed according to one embodiment of the invention. The cassette is constructed of a base member or body 12 and a support or support member 14, each which may be produced by standard molding or machining methods. The support is mounted on the body for movement in a vertical direction in the figures from an at-rest position seen in FIG. 1A to a first sample-transfer position shown in FIG. 1B, and a second sample-transfer position shown in FIG. 1C.

The structure mounting the support on the body may be compressible blocks, such as elastomeric blocks, as shown at 16, which support opposite ends of the support. These blocks become compressed as the support is moved from its at-rest position, where the blocks are substantially uncompressed, to the first and second sample-transfer position, described below, where the blocks are progressively more compressed. It will be appreciated that a variety of compressible structures, such as springs or magnets, could be to mount the support on the cassette body for biased movement toward and away from the sample-transfer position.

Provided within body 12 is a sample well 18 for receiving the body fluid sample to be analyzed. The well is designed to receive a body-fluid sample, such as a blood or serum sample, typically having a volume between about 20 and about 60 µl. The sample well transfers sample to a spreading layer 22 which acts to carry sample liquid from the sample well to the downstream end of layer. Where the sample contains particulate matter, such as blood cells, the spreading layer serves as a separation layer, being constructed to block or retard the movement of sample particles as sample flows through the layer.

Figure 2:
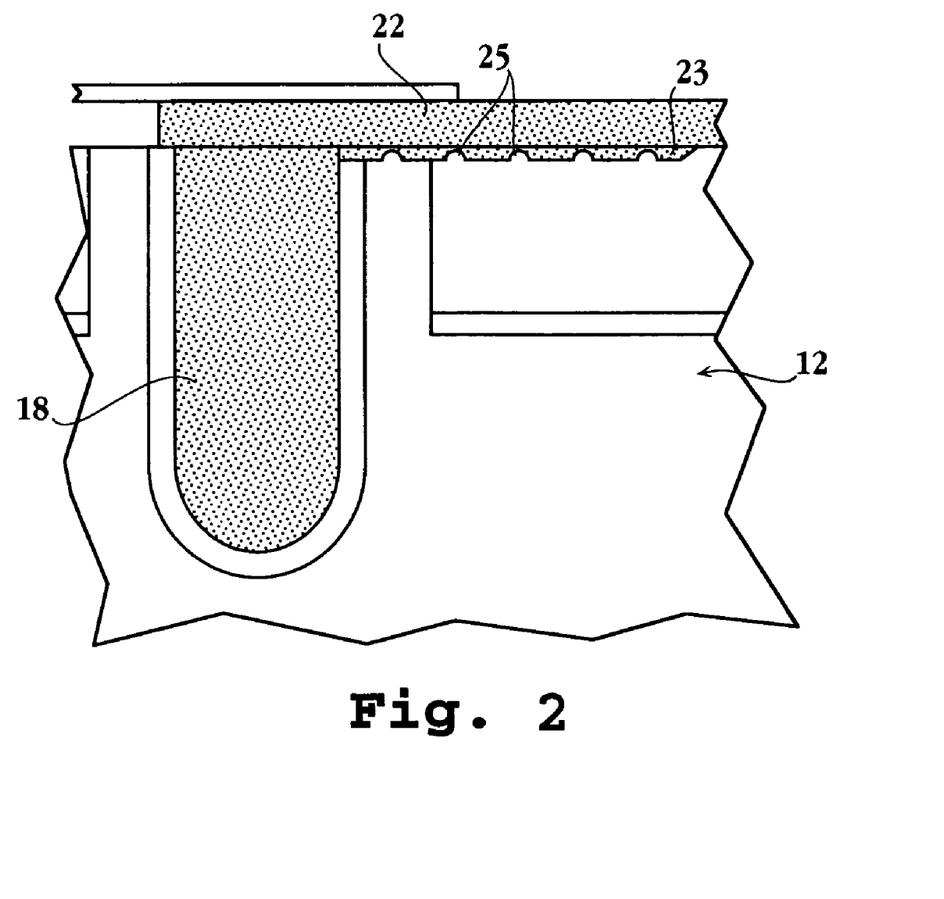
FIG. 2 is an enlarged portion of the cassette shown in the FIG. 1A, in the region of the sample well, showing an undercut channel for enhancing blood flow through the cassette.

In one embodiment, the portion of the cassette body that underlies the upstream portion of the spreading may be undercut, providing a narrow channel or shelf having a thickness of typically 5-15 microns between the cassette body and separation layer, and more typically about 2-5 times the size of the sample particles. This channel, which is indicated at 23 in the expanded FIG. 2, communicates with the sample well, as seen, so that sample fluid applied to the well can migrate unimpeded through this channel underneath the upstream portion of the spreading layer, effectively increasing the area of the spreading layer in contact with the sample, as sample migrates into the spreading layer. The increased area has been found to significantly increase the rate of flow of blood sample through the spreading layer, presumably due to reduced clogging within the region of sample entry into the layer. The bottom of the undercut or channel region may be textured or provided with surface relief, such as the surface bumps shown at 25, to support the spreading layer above the surface of the undercut.

Although not shown here, the cassette may further include a reagent pad disposed between the sample well and the separation layer, for introducing one or more reagents into the sample, during sample flow through the pad into the separation layer. For example, the reagent pad may include reagents such as dextran sulfate for selectively precipitating certain lipoproteins, such as LDL and VLDL particles, allowing selective removal of these particles in an assay to determine HDL cholesterol. In the alternative, such reagents may be applied to the upstream region of the spreading layer.

When sample liquid is placed in well 18, it migrates by capillarity through the spreading layer (and the reagent pad if one is present) in a downstream direction toward the right in the figure. The rate of flow of sample material through the separation layer will depend on the presence and concentration of particulate material in the sample. If the sample is particulate-free, e.g., a serum or plasma sample, the migration time through the separation layer may be on the order of a few seconds. If the sample in a whole-blood sample, migration time through the separation layer may be 30-120 seconds, typically about 60-90 seconds. As will be seen below, the cassette construction and operation are designed to accommodate different flow times, depending on the nature of the sample. FIG. 1A shows this sample distribution, represented by a stippled pattern in the sample well and spreading layer.

Where the device is intended for assaying analyte in a blood sample, the spreading layer is preferably a suitable fiber-mat material, such as a glass-fiber layer, effective to retard the flow of blood cells through the layer, producing a chromatographic separation of blood cells as the sample migrates through the layer. Glass fiber and other matrix material suitable for this purpose are well known. Alternatively, or in addition, the spreading layer may be effective to remove undesired sample components through the use of immobilized binding agents, e.g., antibodies, specific against the unwanted components. Undesired sample components can also be removed by exposing the sample to a precipitating agent in the flow path effective to selectively precipitate the undesired sample components. For example, dextran sulfate may be used to selectively precipitate certain lipoproteins in a blood sample, as noted above.

The spreading layer and reagent pad, if present, are preferably formed of bibulous, fibrous material capable of drawing fluid via capillary flow. A variety of fibrous materials, such as are commonly used in fibrous-mat filters, including cellulose, cellulose acetate, and glass fibrous matrices, are suitable materials for the transfer strip. The fibers may be crosslinked, if desired, by chemical crosslinking, heat fusion, or the like. Also suitable are porous substrates, such as sintered glass, fused polymer beads, and the like, whose wettability and dimension of interstices are such as to promote movement of an aqueous medium into the strip by surface wetting. One exemplary material is a glass fiber filter having a packing density of about 0.2-0.5 $gm/cm^3$. The center glass, spreading layer and reservoir may be mounted on the body directly on the body or through a backing made of plastic or other inert support material. The separation layer may contain additives, such as lectin and/or mannitol to assist in removal of red blood cells or other particulate sample components, as is known. The separation layer has a typical length, width, and thickness dimensions of 15-30 mm, 1-5 mm, and 0.1-0.5 mm, respectively, and a total absorption volume of about 20 µl.

Although the cassette embodiment shown is designed for a single assay, at the right side of the cassette in the figures, it will be appreciated that the cassette could be adapted for additional assay(s) at the left side of the cassette. Further, the additional assay may have the same fluid-flow format, or may have a different format, e.g., the sample well may communicate with an elongate reaction strip extending along the upper left edge region of the cassette body.

The downstream end of the separation layer terminates against a reagent-pad assembly 24 also mounted on the cassette body. The assembly includes a support block 26, a reagent or reservoir pad 28 carried on the upper surface of the block and having a overhanging portion 28a disposed above the separation layer, and a wicking strip 30 abutting the end of pad 28 opposite the pad's overhang portion. The reservoir is preferably a absorptive pad capable of drawing imbibing sample liquid by capillarity, when portion 28a is bend downwardly in the figure to bring the end of the portion into contact with the separation layer, as indicated in FIG. 1B. The figure shows the transfer of sample material from the spreading layer to the reservoir when the support is moved to its first transfer position. In a typical embodiment, the reservoir is a Porex™ material (fused plastic bead material) having typical length, width, and thickness dimensions of 3 to 5 mm, 1-5 mm, and 0.1-0.5 mm, respectively, and a total absorption volume of about 4 µl, where a 2 mm portion of the reservoir overhangs the block. The reservoir contains a first reagent composition effective to react with one or more sample components to form a modified sample, as will be described below.

Wicking strip 30, which abuts the downstream end of reservoir 28, acts to wicking sample fluid from the reservoir onto a reagent pad in the cassette, as will be described below. The wicking strip may be any suitable wicking strip material, such as a nitrocellulose strip, and has a typical length, width, and thickness dimensions of 1 to 2 mm, 1-5 mm, and 0.1-0.5 mm, respectively, and a total absorption volume of about 1 µl. The wicking strip, reservoir, and spreading layer are attached to their respective cassette-body structures conventionally, e.g., with an adhesive.

Support 14 has a pair of elongate extensions or bars, such as bar 32, extending outwardly from the center of the support, as seen in FIGS. 1A-1C. An elongate reagent strip 34 is affixed to and extends along the lower, inward-facing surface of the support, as shown. The strip has an upstream sample-transfer zone 36 and a downstream detection zone 38 located directly below a window 40 formed in the support bar. As seen in FIG. 1C, movement of the support to its second sample-transfer position, with additional compression of blocks 16, brings the sample-transfer zone into contact with wicking strip 30, promoting capillary fluid flow from the reservoir to the reagent strip.

The reagent strip is formed of a material porous or fibrous material which promotes capillary flow therethrough. Preferred materials include porous, fused polymer or microporous polymer membranes, such as polysulfone, polypropylene, nylon, nitrocellulose, Teflon™, or polyvinylchloride microporous membranes. In the present case, nitrocellulose, such as is available from Sartorius, is particularly preferred, with such having length, width, and thickness dimensions between 5-20 mm, 1-5 mm, and 0.1-0.5 mm, respectively.

The downstream end of strip 34 is in contact with an absorbent pad 42 which functions as a reservoir to draw sample liquid supplied to the strip at the sample-transfer zone, and flowing in a downstream direction (to the right in the figures) into and through the detection zone. The pad is formed of a suitable absorbent material such as fibrous glass or cellulose. The absorbance volume of the pad is preferably at least half of the volume of the sample added, e.g., 10 to 30 μl.

Disposed within the fluid pathway defined by the reagent strip are reagents, described further below, effective to produce a detectable, analyte-dependent reaction product which is detected at the detection zone. Various assays may therefore be carried out using the cassette, as described below.

The outer-facing surface of the reagent strip, downstream of the sample-transfer zone, is covered by an impermeable reflective film 46, such as a Mylar film. In particular, the film extends over the detection zone in the reagent strip, which is sandwiched between the support window and the reflective film. The purpose of the reflective strip is to enhance the reflectivity of the reagent strip, as viewed through the support window, and in particular, to enhance the change in reflectivity observed when the strip is wetted, and in response to an analyte-specific reaction occurring in the detection zone, as will be discussed further below.

Figure 3:
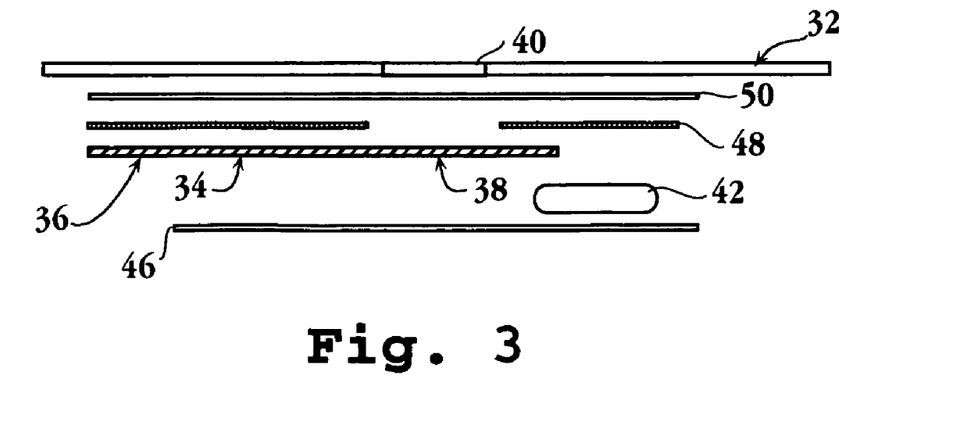
FIG. 3 is an enlarged section view of the cassette support in the region of the detection zone.

The construction of the various layers on the support is illustrated in exploded view in FIG. 3. Shown here are support bar 32 having window 40 located therein, and reagent strip 34 having upstream sample-transfer zone 36 and detection zone 38. The strip is attached to the support bar with a double-side adhesive strip 48 initially covered with a removable backing 50. As shown, the adhesive strip is separated by a space corresponding to the support window and detection zone. Absorbent pad 42 is positioned to overlap with the downstream end of reagent strip 34, and the reflective film 46 is positioned to extend from a point just downstream of the sample-transfer region in strip 34 to a point beyond the absorbent pad. In construction, the components above are arranged as shown, and attached to the support bar and to one another by removing adhesive backing 50 and pressing the adhesive side of the assembly firmly against the support bar.

The cassette is designed particularly for an analyte assay in which (i) sample components, which typically include the analyte itself, react with one or more reagents in the reservoir to form a modified sample, and (ii) the modified sample, typically modified analyte, reacts with a second reagent composition to produce a detectable, analyte-dependent product. That is, both the reagent reservoir and the reagent strip in this preferred embodiment contain one or more reagents for carrying out these reactions. The one or more reagents in the reservoir and strip are also referred to herein as a first and second reagent compositions, respectively, and may include one or more enzymes, antibodies, labeled antibodies, or enzyme substrates, binding agents, and/or precipitation agents, as discussed further below.

In one exemplary cassette, for detection of a multi-valent antigen analyte, the reagent composition in the reservoir includes a non-immobilized analyte-specific antibody labeled, e.g., covalently with a detectable reporter, e.g., metal particles, fluorescent or colored molecules, branched polymers containing attached colored or fluorescent moieties, and coated particles, e.g., fluorescent-coated latex particles. By "non-immobilized" is meant that the reagent is freely mobile within the reservoir. Thus, when analyte is added to the reservoir, it reacts specifically with the antibody reagent to form a mobile, labeled analyte-antibody complex. In other embodiments, the reagent compositions may be immobilized or non-immobilized, depending on whether the reagent must co-migrate with the analyte and/or whether the reagent would be expected to interfere with the final analyte determination.

Methods of labeling a binding agent, such as labeled antibodies, are known in the art, including the use of radiolabels, fluorescent labels, or linked enzymes which convert a separate substrate to a detectable species. A variety of reporter-labeled antibodies, such as enzyme-labeled antibodies, are commercially available or may be readily prepared according to known methods (see, e.g., Harlow, pp. 319-358). Optically detectable labeling methods are preferred for use with the present immunoassay cassette. Enzymes which react with a substrate to produce a visible reaction product are widely used for this purpose. A particularly preferred labeled reagent is an analyte-specific antibody conjugated to a visible particle such as a colored latex bead or colloidal gold. Such conjugates are described in U.S. Pat. No. 4,313,734 (Leuvering) and may also be obtained from manufacturers such as BB International (Cardiff, UK) and NanoProbes (Stony Brook, N.Y.).

The reagent composition in the reagent strip, which may include one or more reagents, may be distributed throughout the strip, or localized on the strip, for example, at the sample-transfer zone, just downstream of the transfer zone, or in the detection zone, in immobilized or non-immobilized form. In the embodiment described above, for detection of a multivalent analyte, the second reagent composition includes an anti-analyte antibody immobilized at the detection zone. In this format, labeled analyte-antibody complex transferred from the reservoir to the reagent strip migrates in a downstream direction in the strip, where it is captured in the detection zone. The step of forming a detectable reaction product includes capturing a detectable complex at the detection zone.

In other embodiments, the second reagent composition may include immobilized or non-immobilized enzymes, substrates, labeled binding reagents, photosensitizer agents, reducing or oxidizing agents, and/or acid or base groups that that can donate protein and hydroxyl ions as part of an analyte-detection reaction, according to known, two-step reaction procedures, where, in the present invention, one of the steps is to be carried out in the reagent reservoir, and the second in the reagent strip.

More specifically, the detection zone may contain reagents effective to produce a detectable reaction product with unlabeled antibody-analyte complex. For example, the detection zone may contain an oxidase, a peroxidase, and a compound oxidizable to a detectable species such as a dye. When the analyte-antibody complex includes a substrate for the oxidase, the $H_2O_2$ generated in the resulting reaction reacts with the oxidizable compound, catalyzed by the peroxidase, to generate the detectable dye. Such assays are described, for example, in Hewett et al.

The reagents may be incorporated into the reservoir and strip by soaking the reservoir or strip material in a solution of the reagents, followed by drying, or adding a solution of the reagent material to the entire or a localized region of the strip, followed by drying. Where the reagent is immobilized, the reservoir or strip region may naturally provide, or be chemically modified according to known methods to have surface reactive groups, such as amine, carboxyl, sulfhydryl, or aldehyde groups, allowing covalent coupling by the use of activating agents or bifunctional coupling agents.

In one particular embodiment, the cassette is designed for detection of C-reactive protein, typically measured in a blood or serum sample. In this embodiment, the reagent composition in the reservoir is a non-immobilized monoclonal antibody specific against a C-reactive protein epitope, i.e., an epitope on one of the 5 identical subunits in C-reactive protein. One exemplary anti-C-reactive protein antibody is a monoclonal antibody produced by cell line identified by clone number CC002, and available from Scripps Laboratories (San Diego, Calif.). The antibody is labeled by conjugation to gold microparticles, according standard methods, e.g., as described in, Chandler, et al., *The place of gold in rapid tests*, IVD Technology, 6(2)37-49 (2000). The second reagent is an antibody specific against C-reactive protein and immobilized at the detection zone. An exemplary antibody is the same as that employed in the first (reservoir) antibody reagent. Details of the assay are given in Example 1.

FIGS. 1A through 1C illustrate the flow of sample liquid into and through the fluid-flow elements of the cassette during cassette operation. As seen in FIG. 1A, liquid sample applied to sample well 18 is drawn by capillarity into the separation strip, and flows along the strip toward its downstream end. Once sample liquid has migrated through the entire spreading layer, the support is moved to its first transfer position, shown in FIG. 1B, to transfer sample liquid from the spreading layer to the reservoir, where the sample components can react with the reagent components in the reservoir. After filling the reservoir, the cassette support is brought to its second transfer position, shown in FIG. 1C, placing the upstream region of reagent strip 34 into contact wicking strip 30, to promote flow of liquid from the reservoir into the reagent strip. From here, the modified sample component produced in the reservoir reacts with the second reagent composition in the reaction strip to form a detectable analyte-dependent product, seen at window 40.

As will now be described, the successive movement of the support from its at-rest position to its first and second transfer positions is timed to (i) ensure filling of each of the fluid-flow pathways in the cassette, before the next fluid-transfer is initiated, and (ii) reduce loss of analyte-related signal in the sample caused by diffusion of analyte components in a back-flow direction, e.g., in an upstream direction. The first objective is achieved by timing the transfer events so that the first transfer occurs only after the spreading layer has been saturated, and the second transfer event occurs only after the reservoir has been saturated. The second objective is achieved by transferring sample fluid from the reservoir into the reaction strip, ideally, as soon as the reaction of sample components with reservoir reagents is complete.

As indicated above, these timing events will be governed largely by the type and amount of particulate matter in the sample, which will determine the rate of flow of sample material through the spreading layer, and thus the flow of sample material from the spreading layer into the reservoir. Where the sample is a particulate-free liquid, such as plasma or serum, the spreading layer may be filled within a few seconds of sample introduction, so the first transfer step can be initiated shortly, e.g., 10-20 seconds ($\Delta t_1$) after sample introduction. Similarly, since sample flow from the spreading layer into the reservoir will also be relatively fast, e.g., on the order of a few seconds, the second transfer step from the reservoir into the reaction layer can be initiated a short time later, e.g., 15 seconds later ($\Delta t_2$), or as soon as the reservoir reaction has had time to run to completion.

By contrast, for a blood sample having a large concentration of blood-cell particulates, flow of sample liquid through the spreading layer may take 30-90 seconds or so, so $\Delta t_1$, the time interval between sample introduction and the first transfer step may be set at 60-90 sec. Similarly, once the spreading layer has filled, the reduced flow rate in the spreading layer will cause relatively slow filling of the reservoir, so $\Delta t_2$ the time interval between the first and second transfers, will also be relatively long, e.g., 30-60 seconds.

When the support in the cassette is moved to its sample-transfer position, shown in FIG. 3C, after the support is moved to its second transfer position, sample liquid flows by capillarity into the strip transfer zone when the latter is brought into contact with the reservoir. From the transfer zone, the sample liquid migrates in a downstream direction into and through the detection zone and ultimately into absorbent pad 42.

In addition to the above mode of operation, the rate of liquid transfer, and the total sample volume transferred from the reservoir to the reaction strip can be controlled by controlling (i) the cycle frequency with which the actuator moves the support toward and away from its transfer position, (ii) the time of contact that the support is held in its transfer position, during each cycle, and (iii) the total number of transfer cycles, as discussed in the next section.

II. Cassette-Handling Instrument

Figure 4:
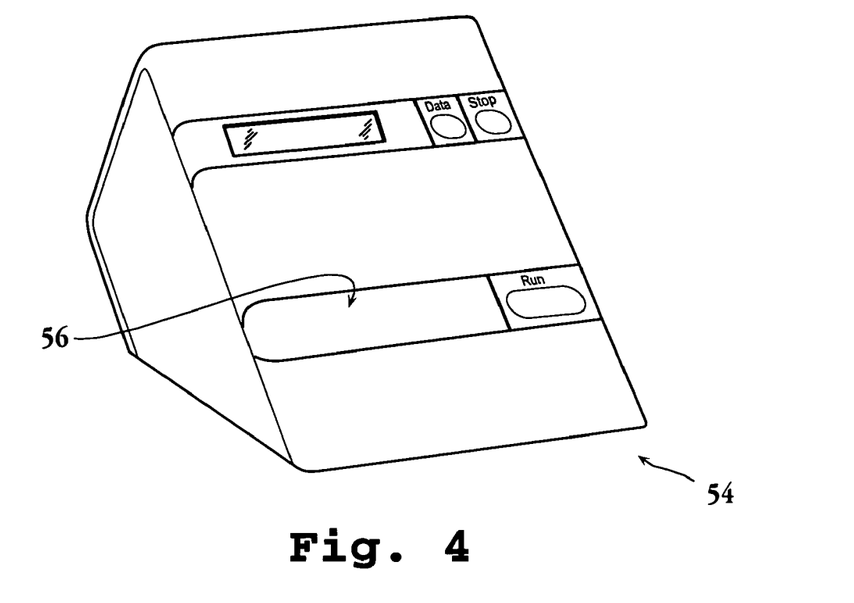
FIG. 4 is a perspective view of a cassette-handling instrument constructed according to one embodiment of the invention.

FIG. 4 is a perspective view of a cassette-handling instrument 54 constructed in accordance with the invention, and FIG. 4 shows key functional elements of the instrument in diagrammatic form. The instrument includes a cassette holder, represented by slot 56, adapted to receive and hold the cassette in an operative condition when a sample liquid has been added to the cassette. In particular, the holder is biased to engage guide notches in the cassette body to anchor the cassette in the holder at a desired position.

Figure 5:
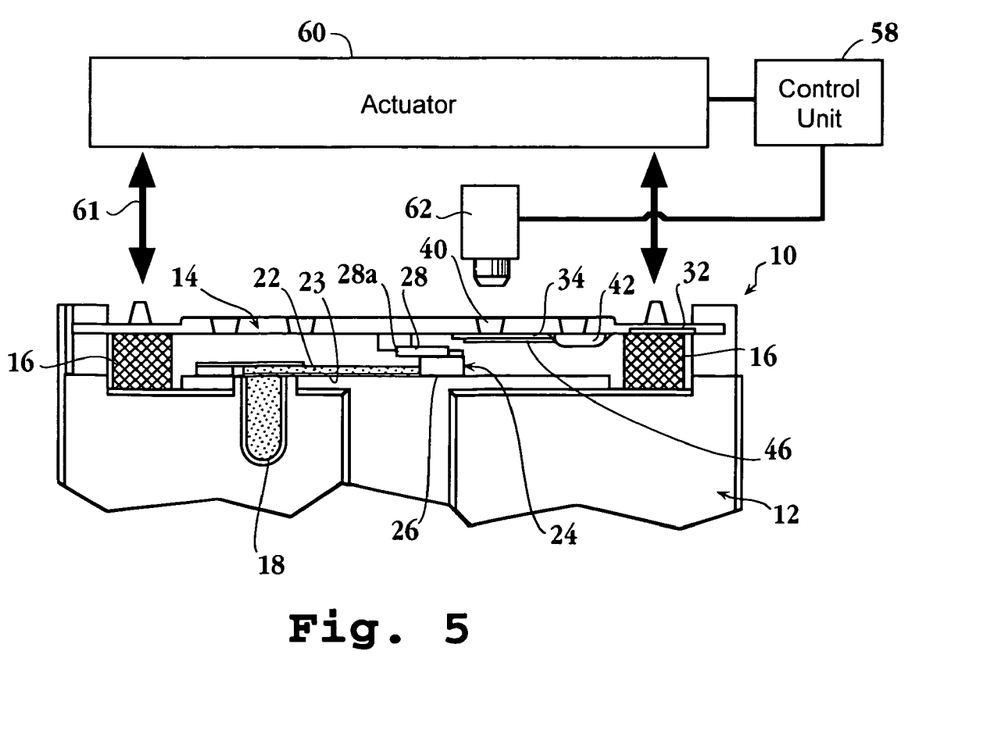
FIG. 5 illustrates various functional components of the cassette-handling instrument in relationship to an immunoassay cassette of the invention.

As seen in FIG. 5, the instrument further includes an actuator 60 having solenoid-activated pistons or pushers, indicated at 61, operable to engage the cassette support and move the support from its relaxed-state to its sample-transfer position, upon actuation from a control unit 58 in the instrument. In particular, the control unit may be programmed or user-adjusted to control the one or more of the following actuator variables:

(i) the period ($\Delta t_1$) between sample addition to the cassette and the first sample transfer, when sample transfer to the reagent reservoir is first initiated. As indicated above, this setting is typically between 10-15 seconds, for a non-particle sample, to 60-90 seconds for a blood sample;

(ii) the period ($\Delta t_2$) between the first and second sample transfers, i.e., the time allotted for sample transfer from the spreading layer to the reagent reservoir. As indicated above, this setting is typically between 10-15 seconds, for a non-particle sample, to 30-60 seconds for a blood sample;

(iii) the cycle frequency with which the actuator moves the support toward and away from its second transfer position, and the duration that the support is held at its second transfer position.

It will be appreciated that the control unit can be preprogrammed to control liquid transfer in the assay in an optimized manner for any selected type of assay chemistry. Various liquid transfer profiles that can be achieved with the invention will be considered below.

Also as shown in FIG. 5, the cassette-handling instrument includes a photo-detector 62, operable to detect changes in the reflectance of the detection zone, as observed through window 40. The photo-detector in this case may be a simple device for measuring the light intensity of reflectance at the window, when the detection window is illuminated by a light source, e.g., an LED, also forming part of the detector. In other embodiments, the detector may include a selected-wavelength fluorescence excitation beam and emitted-light detector, or a selected-wavelength visible light source and photo-detector for measuring light absorption at the detection surface.

Particularly where the light detector is designed to measure reflectance from the reagent strip surface in the detection zone, the reflective film is effective to enhance, i.e., amplify the reflectance intensity, and thus improve resolution and accuracy. As will be seen in the next section, the enhanced reflectance also allows the detection zone to serve as a "control" to monitor fluid flow through the reagent strip.

III. Performance Characteristics

As noted above, one feature of the invention is the ability to control the timing of transfer of sample liquid during cassette operation, to optimize liquid flow and residence times during an assay operation. The invention also provides the ability to control the rate and volume of fluid flow from one reaction area to another, and thus the kinetics of the reactions and the total assay volume. This feature is important where one or more of the assay reactions are rate-limiting or where it is desired to assay a kinetic end point. The feature is also important in controlling the total amount of sample liquid that flows into and through the detection zone, for quantitating the concentration of analyte in the zone.

Figure 6A:
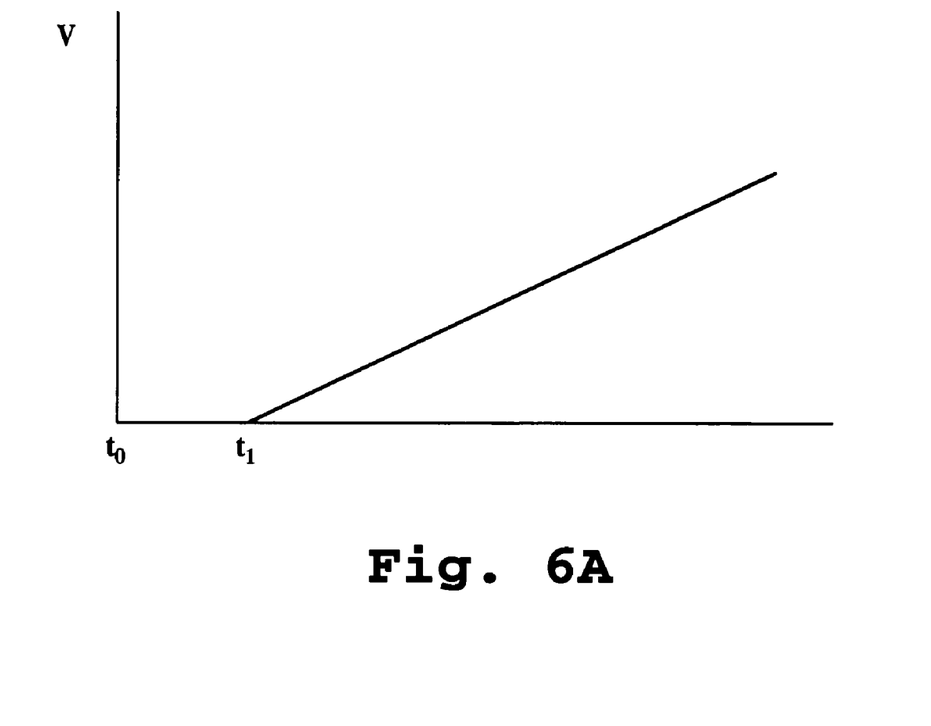
FIGS. 6A and 6B illustrate different sample-volume transfer profiles achievable by the invention.
Figure 6B:
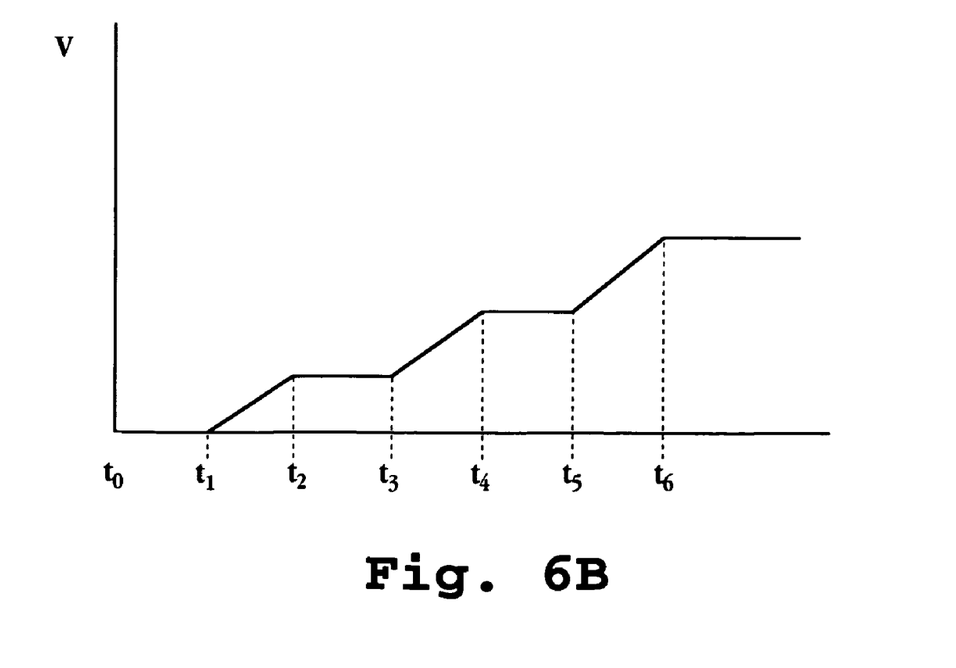

FIGS. 6A and 6B illustrate two sample transfer curves that illustrate the different sample transfer characteristics that can be achieved in the invention. The first case (6A) shows the rate of sample volume accumulation in the reaction strip when the device is operated in a mode in which the cassette support is moved to its second transfer position, at time $t_1$, and held there over an extended period while sample fluid migrates from the reagent reservoir to the reaction strip. In FIG. 6B, the sample incubation time, from $t_1$ to $t_2$, is the same as in FIG. 6A, but sample transfer is effected by three discrete transfer events, interspersed with intervals in which the support is move out of contact with the reservoir and volume accumulation over time is flat. As can be appreciated, the latter approach allows a more controlled, and typically slower rate of volume transfer than when sample transfer occurs as an unbroken event.

Figure 7:
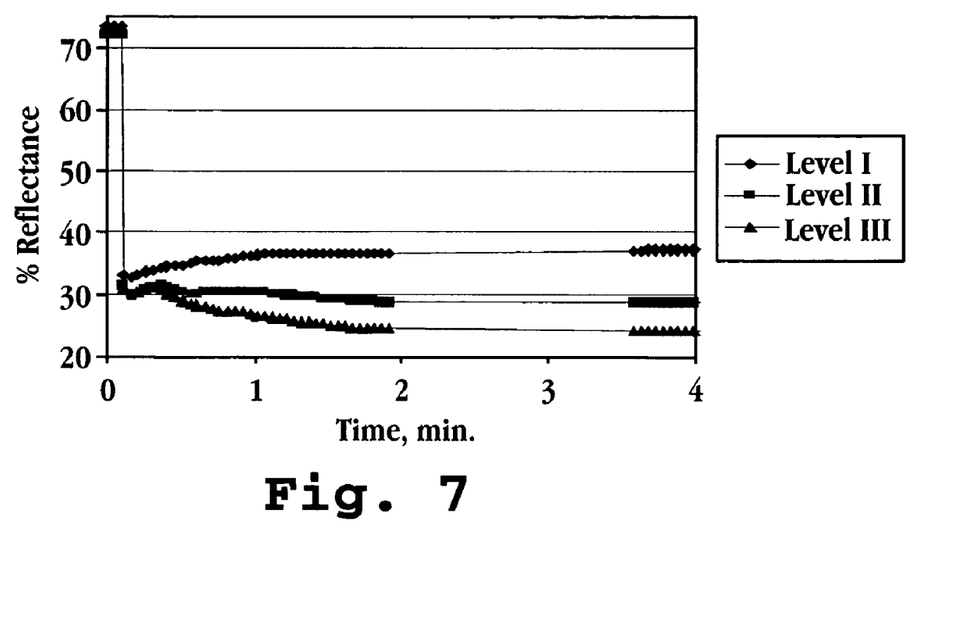
FIG. 7 illustrates reflectance profiles for a C-reactive protein analyte at three different concentrations, during an assay procedure in accordance with one embodiment of the invention.

FIG. 7 shows an exemplary reflectance curve for an assay in which C-reactive protein analyte reacts first with labeled anti-analyte antibody in the cassette reservoir, to form a detectable analyte-antibody complex, and the complex is then transferred to the reagent strip, where it is captured by an immobilized anti-analyte antibody in the detection zone. The initial reflectance, in the first few seconds after sample transfer to the support, corresponds to a dry strip reflectance. The precipitous drop in reflectance occurs when the leading edge of the transferred sample passes through the detection zone. The drop in reflectance is due both to the wetting of the strip in the detection zone and the presence of colloidal gold labeled antibodies, either in complexes or non-complexed form.

With continued flow of sample material through the detection zone, the level of reflectance begins to change over time, depending on the relative concentrations of complexed and non-complexed antibody conjugate, i.e., depending on the sample analyte concentration. At lower analyte concentration, where relatively more of the conjugate is in non-complexed form, and relatively less of the conjugate is captured at the detection zone, the reflectance begins to increase over time as more and more of the conjugate is carried out of the detection zone by sample transfer through the zone. This is seen in the "diamond" plot in FIG. 7. Conversely, at higher analyte concentrations, progressively more conjugate is captured in the detection zone, with sample flow through the zone, acting to decrease reflectance over time, as indicated for the "triangle" plot in the same figure.

The analyte concentration is measured by comparing the measured reflectance at a selected end point, e.g., 4 minutes, with standard reflectance measurements from known analyte concentrations. The measured reflectance may be expressed, for example, as a ratio of the final percent reflectance to initial percent reflectance. As seen in the plot shown in FIG. 8, a plot of this ratio shows an analyte-dependent curve over a C-reactive protein concentration of 0 to 8 µg/ml.

From the foregoing, it can be appreciated how various objects and features of the invention are achieved. The cassette provides a dry-strip assay format in which successive analyte-dependent reactions can be carried out in a controlled manner, by controlling sample transfer events to accommodate different sample flow rates and, optionally, volume and rate transfer from the reservoir to the support strip. The cassette format is amenable to multiple assays in the same cassette, and fed from the same sample. The reflector strip in the support bar acts to enhance reflectance changes, enhancing the reliability and resolution of an assay. Finally, the separation-strip channel feature allows for enhanced flow of blood through the strip.

Preferably, the cassette of the invention is supplied with solutions and reagents preloaded and is thus entirely self-contained, not requiring operator loading of solutions. The reader containing the cassette may be programmed to adjust the cassette to its different operational positions at designated times. A multiple-stage assay may thus be carried out with the cassette contained within a cassette reader, requiring no outside operator input.

IV. EXAMPLES

Example 1

Assay for C-Reactive Protein

In a specific application of the present device, a blood sample was analyzed for levels of C-reactive protein. Altered levels of this compound have been shown to be diagnostic of disorders characterized by risk factors for cerebral vascular ischemia and stroke, and ischemic heart disease and stroke (see, for example, De Maat, Grau, Kuller, Liuzzo, Mendall, Thompson, and Tracy).

The cassette for the assay was prepared as follows: The spreading layer was also glass fiber. The reservoir was a porous plastic material having a total absorption volume of about 3.6 μl. The reservoir was initially soaked with 3.6 μl of a 20 O.D. solution of antibody conjugate formed by conjugating colloidal gold with antibody specific against C-reactive protein, obtained from BB International (Cardiff, UK). The reservoir was then dried.

The reagent strip in the cassette was an 11 mm by 3 mm nitrocellulose strip, obtained from Sartorius (Goettingen, GmbH), having a thickness of less than 10 mils (0.25 mm). The antibody against C-reactive protein was attached to the detection region through hydrophobic interaction with the nitrocellulose. The detection region was located about 6 mm from the sample-transfer region. The absorption pad at the downstream end of the strip was a cellulose fiber material, having a total absorption volume of about 25 μl.

Figure 8:
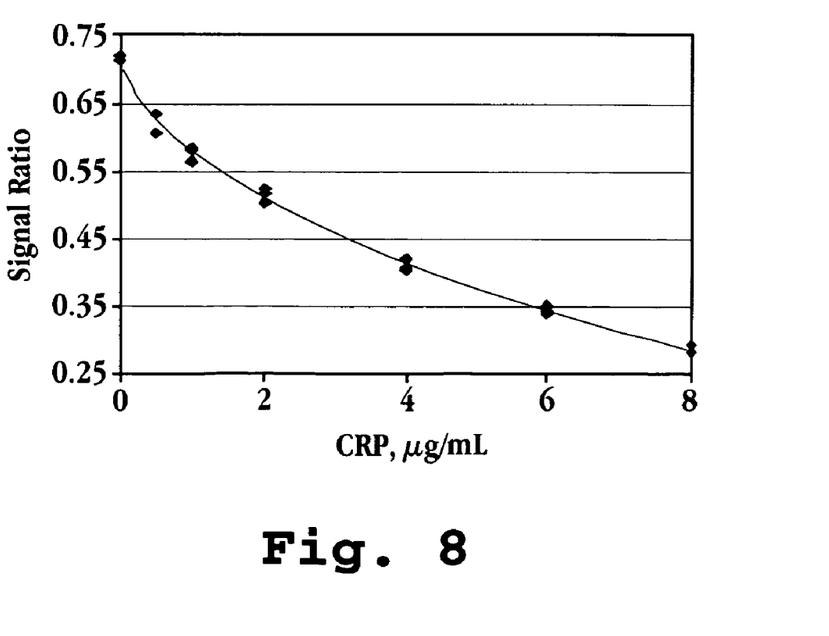
FIG. 8. is a plot of measured reflectance as a function of C-reactive protein analyte concentration, generated in accordance with the invention.

In the assay method, a 50 μl human blood sample was applied to the sample well in the cassette. After a sample transfer period of about 45 sec, the support was moved to its first sample-transfer position for 30 sec. During flow of sample liquid onto the strip, the reflectance at the support-bar window was monitored. At about 4 minutes post sample addition, a stable end point was reached (FIG. 8). The signal ratio of end-point reflectance to initial reflectance was determined and used to calculate analyte concentration from a standard curve generated by samples with known amounts of C-reactive protein.

While the invention has been described with reference to specific methods and embodiments, it will be appreciated that various modifications may be made without departing from the invention.

It is claimed:

1. An immunoassay cassette for use in detecting an analyte in a liquid body fluid sample, comprising:
    (a) a cassette body having a sample well for receiving said sample;
    (b) carried on said body, a reservoir containing a first reagent composition effective to react with one or more sample components to form a modified sample,
    (c) a support mounted on said body, for movement relative to said cassette body to first and second transfer positions, and
    (d) carried on said support, a reagent strip containing a second reagent composition effective to react with the modified sample formed in said reservoir to form a detectable analyte-dependent product,
    wherein movement of support relative to the cassette body to its first transfer position is effective to transfer sample liquid placed in the sample well to said reservoir, and movement of the support to its second transfer position is effective to transfer sample liquid in said reservoir to said reagent strip.

2. The cassette of claim 1, which includes a separation layer mounted on said body in liquid communication with the sample well, and said reservoir is mounted on said body for movement to a position of liquid communication with said separation layer, when the support is moved to its first transfer position.

3. The cassette of claim 2, wherein said separation layer is effective to remove blood cells from a blood-cell sample placed in said sample well, as sample liquid flows in said layer from the sample well toward the position at which liquid is to be transferred to said reservoir.

4. The cassette of claim 1, which includes a liquid-carrying strip carried on said body, abutting one end of said reservoir, and dimensioned to make contact with said reagent strip, for transferring liquid from the reservoir to the reagent strip, when the support is moved to its second transfer position.

5. The cassette of claim 1, for detecting a multivalent analyte in a liquid body-fluid sample, wherein the first reagent composition in the reagent reservoir includes a non-immobilized conjugate of an anti-analyte antibody and a detectable reporter group, the reaction to form a modified sample includes binding of the conjugate to sample analyte, to form an analyte-conjugate complex, the reagent composition in the reagent strip includes an anti-analyte antibody immobilized at a detection region in the reagent strip, and the reaction to form a detectable analyte-dependent product includes binding of complex to the immobilized antibody, to localize the detectable reporter in the complex at the detection zone.

6. The cassette of claim 5, wherein said non-immobilized conjugate is a conjugate of an anti-analyte antibody and a detectable reporter selected from the group consisting of metal particles, particles labeled with colored or fluorescent moieties, polymers labeled with colored of fluorescent moieties, particles, and colored or fluorescent molecules.

7. The cassette of claim 5, for use in detecting C-reactive protein analyte in a blood sample, wherein the anti-analyte antibody in the non-immobilized conjugate in the reagent reservoir, and the immobilized anti-analyte antibody in the reagent strip are antibodies specific against a common epitope in C-reactive protein.

8. The cassette of claim 1, wherein said support includes a window through which a detectable reaction at a detection zone in the reagent strip be viewed, and the detection zone in the reagent strip is covered by a reflective film at the strip's surface facing away from said window, such that flow of sample liquid through the detection zone produces a first change in reflectance measurable through the window, and the presence of analyte-dependent reaction at the detection zone produces a second change in reflectance measurable through the window.

9. The cassette of claim 1, which further includes an absorbent reservoir carried on said support, downstream of said detection zone, and in fluid-flow communication with said strip, for receiving sample liquid transferred onto the reagent strip.

10. An apparatus for use in detecting an analyte in a liquid body-fluid sample, comprising:
    A) a cassette having
        (a) a cassette body having a sample well for receiving said sample;
        (b) carried on said body, a reservoir containing a first reagent composition effective to react with one or more sample components to form a modified sample,
        (c) a support mounted on said body, for movement relative to said cassette body, to first and second transfer positions, and
        (d) carried on said support, a reagent strip containing a second reagent composition effective to react with the modified sample formed in said reservoir to form a detectable analyte-dependent product, and
    (B) a cassette handling instrument having
        (a) a cassette holder into which the cassette is removably placed, during a sample assay, (b) an actuator operable to move the support in the cassette to its first and second transfer positions, (c) a detector operable to detect an analyte-specific reaction at a detection zone in the reagent strip, and (d) a control unit operably connected to the actuator, for moving the support in the cassette to its first transfer position, and subsequently to its second position at timed intervals.

11. The apparatus of claim 10, wherein said actuator is operable to press on one or more surface regions of said support, to move the support toward said cassette body.

12. The apparatus of claim 10, wherein said cassette includes a separation layer mounted on said body in liquid communication with the sample well, and said reservoir is mounted on said body for movement to a position of liquid communication with said separation layer, when the support is moved to its first transfer position.

13. The system of claim 12, wherein said control unit is operable to move said support to its first position at a selected time interval $\Delta t_1$ after sample is introduced into said sample well, and to move the support to its second transfer position, at a selected time interval $\Delta t_2$ later, where $\Delta t_1$ is selected to allow sample-liquid flow from said sample well through said separation layer to the position of liquid communication with the reservoir, and $\Delta t_2$ is selected to allow sample-liquid flow from said separation strip into said reservoir.

14. The cassette of claim 13, wherein said separation layer is effective to remove blood cells from a blood-cell sample placed in said sample well, as sample liquid flows in said layer from the sample well toward the position at which liquid is to be transferred to said reservoir, and $\Delta t_1$ and $\Delta t_2$ are selected to have greater values for a sample containing blood cells than one without blood cells.

15. The system of claim 12, wherein said control unit is further operable to move said support, after time interval $\Delta t_2$, toward and away from its second transfer position, to reduce the volume and rate of sample flow from the reservoir to the reagent strip relative to that obtained when the control unit operates to hold the support at its second transfer position.

16. The apparatus of claim 15, wherein the control unit is operable to control the rate of sample transfer from said reservoir to the reagent strip by controlling (i) the cycle frequency with which the actuator moves the support toward and away from its second transfer position and (ii) the time of contact that the support is held in its second transfer position, during each cycle.

* * * * *